United States Patent [19]
Ryan et al.

[11] 3,967,321
[45] July 6, 1976

[54] ELECTRICALLY DRIVEN HAND ORTHOSIS DEVICE FOR PROVIDING FINGER PREHENSION

[75] Inventors: John Patrick Ryan, Indianapolis; James Walter Cowan, Oaklandon; Paul Kent Sharp; Marilyn Elaine Fess, both of Indianapolis; James L. Babcock, Brownsburg, all of Ind.

[73] Assignee: Indiana University Foundation, Bloomington, Ind.

[22] Filed: Feb. 5, 1975

[21] Appl. No.: 547,272

[52] U.S. Cl. .................................. 3/1.1; 128/77
[51] Int. Cl.² .................. A61F 1/00; A61F 5/10
[58] Field of Search ............... 3/1.1, 1.2, 1; 128/77, 128/26, 88

[56] References Cited
UNITED STATES PATENTS

| | | | |
|---|---|---|---|
| 2,893,016 | 7/1959 | Zion | 3/1 |
| 3,020,908 | 2/1962 | Daniels et al. | 3/1.2 |
| 3,418,661 | 12/1968 | Allison et al. | 3/1.1 |
| 3,548,419 | 12/1970 | Katsuren | 3/1.1 |

FOREIGN PATENTS OR APPLICATIONS

| 2,110,237 | 9/1971 | Germany | 3/1.1 |
|---|---|---|---|

OTHER PUBLICATIONS

"Development of Useful Function in the Severely Paralyzed Hand," by V. L. Nickel et al., The Journal of Bone & Joint Surgery, vol. 45-A, No. 5, July 1963, pp. 933–952.
"Electrically Powered Orthotic Systems," by V. L. Nickel et al., The Journal of Bone & Joint Surgery, vol. 51-A, No. 2, Mar. 1969, pp. 343–351.

Primary Examiner—Ronald L. Frinks
Attorney, Agent, or Firm—Kirkland & Ellis

[57] ABSTRACT

The arm splint of an orthosis is attached to the forearm of a cervical 6 - cervical 7 motor lesion quadraplegic. The arm splint includes a thumb flange for holding the thumb of the patient, and a pivoting finger trough for holding the first and middle fingers of the patient. A Bowden cable is connected to the pivoting finger trough and is operated by a motor to cause the pivoting finger trough to pivot to close towards the thumb flange to provide finger prehension so that the patient can grasp objects. The motor is controlled by control circuitry that is operated by the patient touching a touch sensitive contact that is typically mounted on the arm rest of a wheelchair. The control means and the motor are powered by a twelve-volt car battery carried on the wheelchair. The control means also includes a time delay so that the patient can operate the control means by touching the touch sensitive contact and then move the arm and hand to a position ready for grasping. Subsequent contact with the touch sensitive contact results in reverse operation of the motor so that the grasped object can be released.

20 Claims, 12 Drawing Figures

ELECTRICALLY DRIVEN HAND ORTHOSIS DEVICE FOR PROVIDING FINGER PREHENSION

BACKGROUND OF THE INVENTION

1. Field of the Invention

The present invention relates to a hand orthosis or orthopedic device for providing finger prehension for a cervical 6 — cervical 7 motor lesion quadraplegic.

2. Description of the Prior Art

If a human motor nerve is injured, the effect is to cut-off the output signals from the spinal chord and higher centers to the effector tissues (the muscles) which the injured nerve supplied. Very limited and circumscribed lesions in the spinal chord may involve a motor or sensory side of the input-output system with loss of motor control. Spinal chord injuries may be partial or complete, and location of the injury determines the extent of the loss of motor control. Typically, cervical 6 — cervical 7 motor nerve lesions result in loss of motor control of the legs and portions of the arms. However, typically, depending on the extent of the injury, a cervical 6 — cervical 7 motor lesion quadraplegic retains some control over the movement of the arms but loses control over movement of the hands and fingers. Thus, while the cervical 6 — cervical 7 motor lesion quadraplegic can move his or her arm, it is impossible to grasp objects with the fingers.

An orthosis or othetic device is a brace or other orthopedic device which is applied to the body in the treatment of physical impairment or disability. Orthopedic devices to control and operate a paralysed hand to permit the paralysed hand to pick up articles and objects are known in the art. For example, U.S. Pat. No. 2,553,277 - Robinson et al., discloses a control and operating means for paralyzed hands. In addition, U.S. Pat. No. 2,893,016 – Zion discloses a prosthetic device forming an artificial hand for use by the patient whose hands do not function normally. Further, U.S. Pat. No. 3,707,963 – Keropian discloses an articulated hand brace for articulating a disabled or paralyzed hand.

Various other prosthetic and orthopedic devices are well known in the art. However, one problem experienced with prior art prosthetic and orthotic devices is providing a control mechanism that is easily operable by the patient. Typically, quadraplegics and other disabled individuals have a very limited ability to provide the necessary muscular control to activate a mechanism to control the prosthetic or orthotic device. For example, U.S. Pat. No, 3,769,636 — Friedman discloses an orthotic brace using the head orientation of the patient to control the device. Thus, by movement of the patient's head in various directions, the articulation of the device is controlled. However, this device is relatively expensive and unnecessary where the patient has some muscular control of the arm such as in the case of a cervical 6 - cervical 7 quadraplegic.

Similarly, U.S. Pat. No. 3,683,423 — Krapanzano discloses a gravity actuated prosthetic device utilizing a control mechanism using gravity sensitive mercury switches for control purposes. However, this device is dependent upon the position and orientation of the prosthetic device itself to initiate operation of the device which may not be compatible with the activity desired by the patient.

Orthopedic and orthotic devices are typically designed so that the patient operates the device with the arm opposite the arm being controlled. This limitation prevents the patient from being equipped with such an orthotic device on each arm and hand so that each hand can be controlled.

Thus, it would be a desirable advance in the art to provide a hand orthosis for providing finger prehension for a cervical 6 - cervical 7 motor lesion quadraplegic that can be controlled by the same arm to which the device is attached so that the patient may be equipped with an orthosis for each arm. Further, it would be a desirable advance in the art to provide an activating means for such an orthosis which will require no force from the patient to initiate operation. In addition, since a cervical 6 - cervical 7 motor lesion quadreplegic is typically equipped with a battery operated wheelchair for movement, it would be a desirable advance in the art to provide an orthosis which can be attached to the wheelchair and powered by the same battery as the wheelchair.

DESCRIPTION OF THE INVENTION

A hand orthosis for providing finger prehension for a cervical 6 - cervical 7 motor lesion quadraplegic in accordance with the present invention comprises an arm splint means for attachment to the patient's forearm which includes a means for retaining the patient's thumb and means for retaining at least one finger of the patient. Additionally provided is means for providing prehension of the thumb and at least one finger of the patient so that the patient can grasp objects between the thumb and finger. Control means are provided for operating the arm splint means to cause the prehension of the thumb and finger of the patient so that the patient can grasp and release objects.

Touch sensitive contact means for causing the control means to operate in response to touch contact by the patient is provided so that the patient can initiate operation of the device without force with the same arm to which the arm splint means is attached. Typically, the touch sensitive contact means is attached to the arm rest of a wheelchair, and the control means is mounted on the wheelchair and powered by the same 12 volt battery as powers movement of the wheelchair.

The control means also includes a time delay means which permits the patient to initiate operation of the control means by touching the touch sensitive contact means and then move the arm and hand to a position ready for grasping the desired object. The control means is also adapted to cause reverse operation of the arm splint means in response to a subsequent touch by the patient of the touch sensitive contact means.

More particularly, the arm splint means comprises a forearm trough that is adapted to be placed around the forearm of the patient and a thumb flange and a finger trough for retaining the thumb and first and second fingers of the patient. The finger trough is pivotably mounted so that pivoting of the finger trough causes the patient's fingers to move toward and away from the thumb. A Bowden cable is connected to the finger trough and to a motor so that operation of the motor in one direction causes the fingers to move towards one another and operation of the motor in the other direction permits a spring bias means to open the fingers.

Thus, it is a primary object of the present invention to provide a hand orthosis for providing finger prehension for a cervical 6 - cervical 7 motor lesion quadraplegic that is operated by a touch sensitive contact that may be touched by the patient to initiate operation without requiring undue force or complicated muscular articulation by the patient to initiate operation.

It is a further object of the present invention to provide a hand orthosis that can be controlled and operated by the same arm to which the device is attached so that the patient can be equipped with such an orthosis for each arm.

A further object of the present invention is to provide a hand orthosis that provides a time delay so that the patient can initiate operation of the device and then prepare to grasp an object.

Yet another object of the present invention is to provide a hand orthosis that can be mounted on a battery powered wheelchair and operated by the same battery that operates the wheelchair.

These and other objects, advantages, and features will hereinafter appear, and for the purposes of illustration, but not of limitation, exemplary embodiments of the present invention are illustrated in the accompanying drawings.

DETAILED DESCRIPTION OF THE PREFERRED EMBODIMENT

Figure 1:
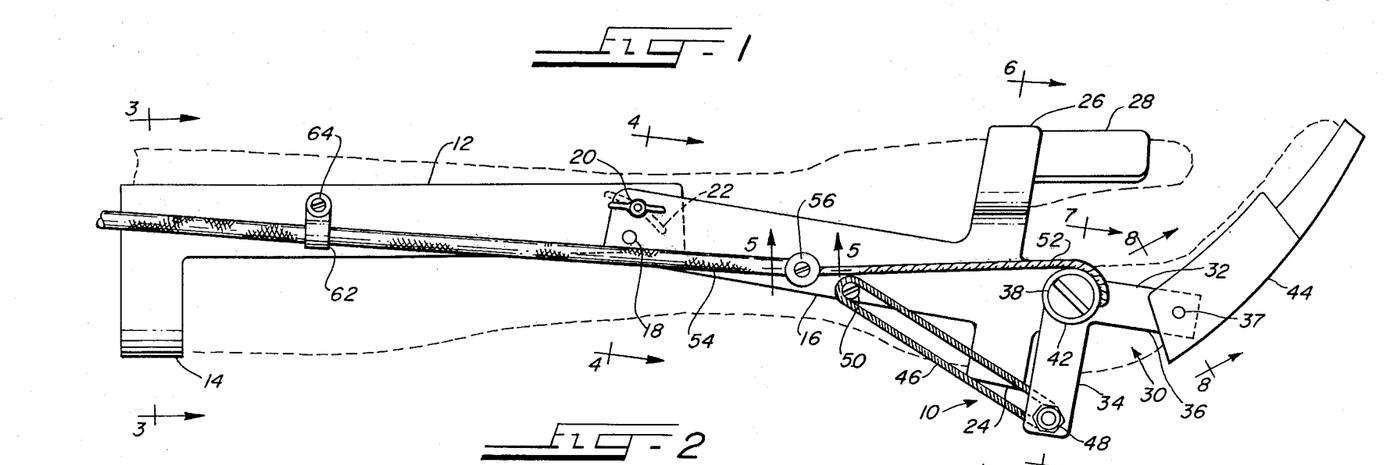
FIG. 1 is a top view of the arm splint of the present invention.
Figure 2:
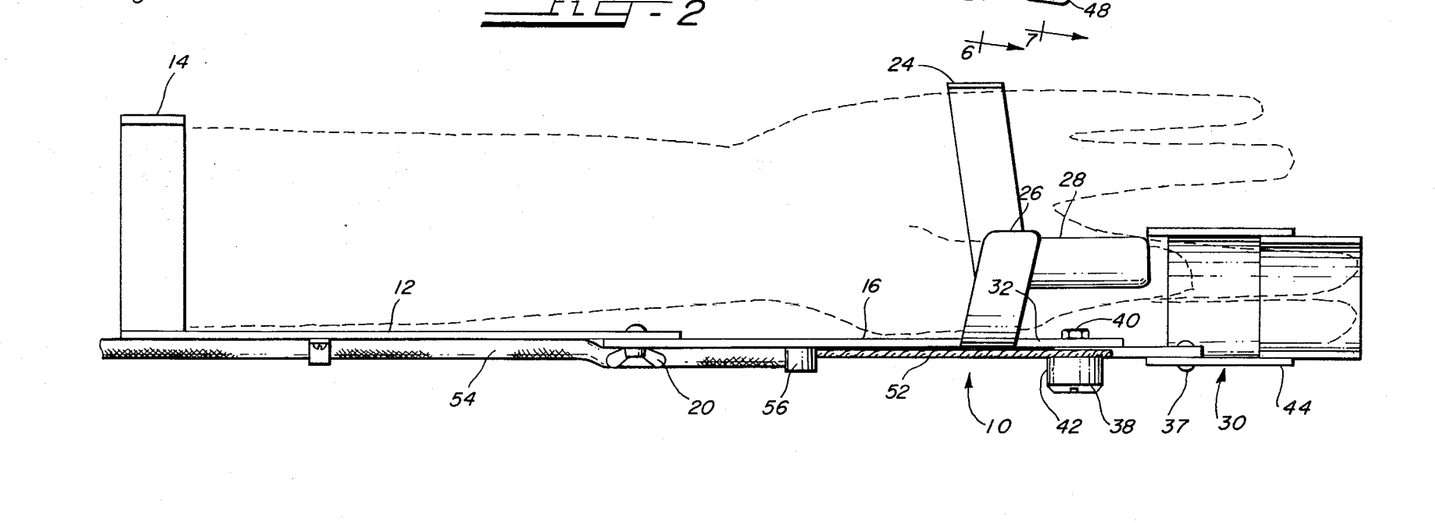
FIG. 2 is a side view of the arm splint illustrated in FIG. 1.
Figure 3:
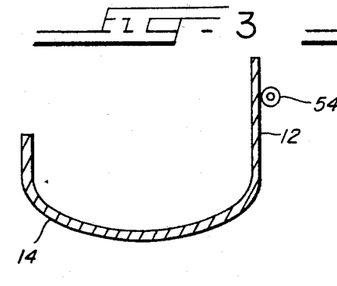
FIG. 3 is a cross-sectional view taken substantially along line 3—3 in FIG. 1.
Figure 4:
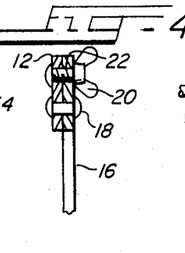
FIG. 4 is a cross-sectional partially fragmentary view taken substantially along line 4—4 in FIG. 1.

With reference to FIGS. 1 and 2, arm splint 10 comprises arm trough member 12 having an arm cradle flange 14 that is curved to fit around the forearm of the patient (see FIG. 3). To facilitate understanding of the present invention, a representation of a patient's arm and hand is illustrated in FIGS. 1 and 2 by dotted lines. Arm trough member 12 may be attached to the patient's arm by a strap, tape or any other suitable means. Pivotably attached to the arm trough member 12 is a hand trough member 16. Hand trough member 16 is pivotably mounted to arm trough member 12 by pin 18 and wing nut 20. Wing nut 20 extends through a slot 22 (shown by dotted lines in FIG. 1) so that when wing nut 20 is loosened, hand trough member 16 may be pivoted about pin 18 to adjust the angular relationship between the arm trough member 12 and the hand trough member 16.

Figures 6, 7, 8, 9:
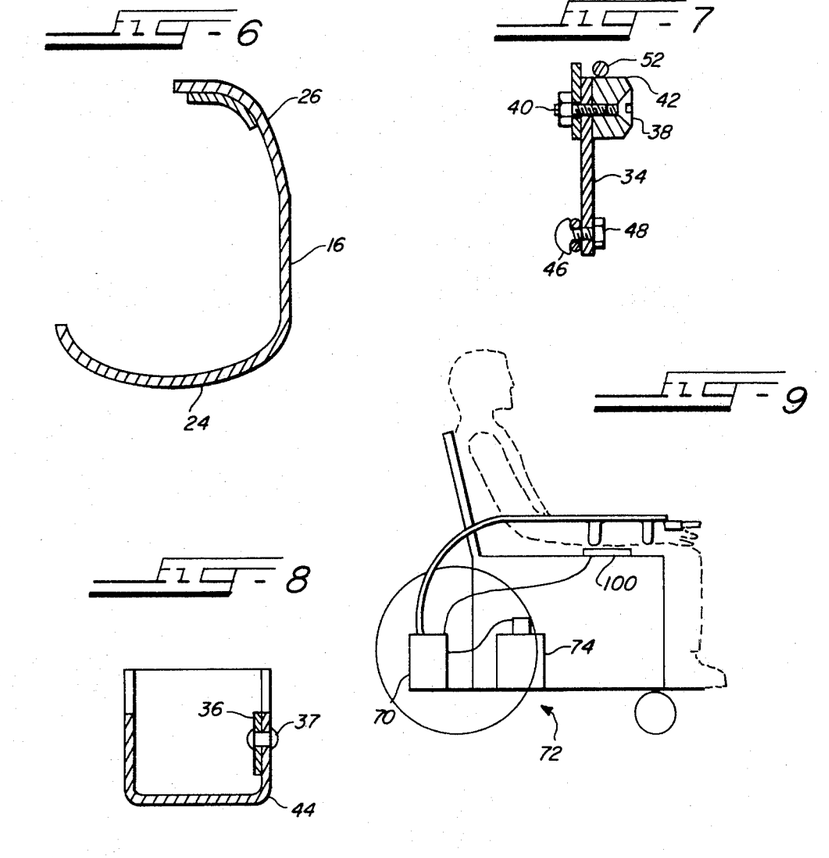
FIG. 6 is a cross-sectional view taken substantially along line 6—6 in FIG. 1.
FIG. 7 is a cross-sectional view taken substantially along line 7—7 in FIG. 1.
FIG. 8 is a cross-sectional view taken substantially along line 8—8 in FIG. 1.
FIG. 9 is a graphic representation of a patient in a wheelchair to which the present invention has been mounted.

Connected at the other end of hand trough member 16 is a hand cradle flange 24 that is formed to support the back of the patient's hand (see FIG. 6). The patient's hand may be attached to hand trough member 16 by a strap, tape, or any other suitable means.

Also formed at the end of hand trough member 16 is thumb trough flange 26. Extending from thumb trough flange 26 is thumb support member 28. Thumb trough flange 26 and thumb support member 28 are formed to retain the thumb of the patient in a normal position. The patient's thumb may be attached to thumb support member 28 by a strap, tape, or any other suitable means.

Also pivotably mounted to the end of hand trough member 16 is finger trough assembly 30. Finger trough assembly 30 comprises L-shaped member 32 having two arms 34 and 36 extending approximately perpendicular to one another. L-shaped member 32 is pivotably mounted to hand trough member 16 by screw 38 and bolt 40. Screw 38 extends through annular member 42 that is rigidly affixed to L-shaped member 32 (see FIG. 7).

Rigidly attached to the end of arm 36 by rivet 37 is finger trough member 44 that is formed to retain the first and second fingers of the patient. A strap, tape or any other suitable means may be used to retain the fingers in finger trough member 44.

A spring 46 is attached to the end of arm 34 by a bolt 48, and the other end of spring 46 is attached to hand trough member 16 by a screw 50. Spring 46 normally biases finger trough assembly 30 in a clockwise direction as viewed in FIG. 1 so that the fingers and thumb of the patient are normally positioned in an open position.

Figure 5:
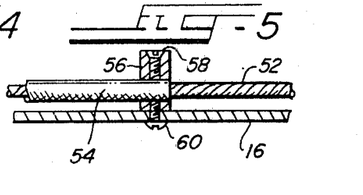
FIG. 5 is a cross-sectional partially fragmentary view taken substantially along line 5—5 in FIG. 1.

Partially wrapped around annular member 42 and attached to one end by any suitable means is a cable 52. Cable 52 extends along hand trough member 16 and enters the hollow interior of flexible annular sleeve 54 so that cable 52 can slide within flexible annular sleeve 54. Flexible annular sleeve 54 is attached at one end to hand trough member 16 by fitting 56, screw 58 and screw 60 (see FIG. 5) so that the end of flexible annular sleeve 54 cannot move. Flexible annular sleeve 54 is also held to arm trough member 12 by flange 62 and screw 64. Cable 52 and flexible annular sleeve 54 are typically referred to in the art as a Bowden cable.

Figure 10:
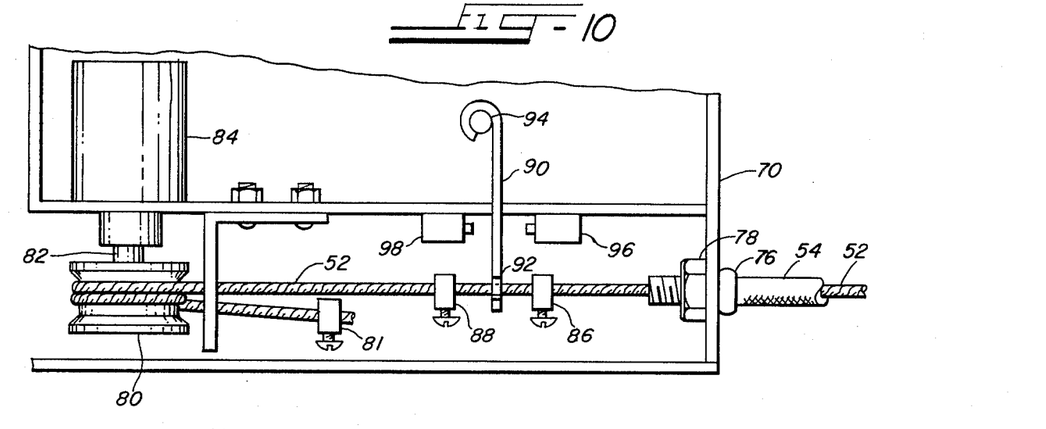
FIG. 10 is a side partially fragmentary view of the motor and limit switch arrangement of the present invention.

With reference to FIGS. 9 and 10, control housing 70 is mounted to a conventional wheelchair 72 having a conventional twelve volt automobile battery 74 mounted thereon for driving the wheelchair. Sleeve 54 extends to control housing 70 and the end of sleeve 54 is rigidly attached to the wall of control housing 70 by fitting 76 and bolt 78. Cable 52 extends into control housing 70 and is wrapped around a pulley 80 mounted on shaft 82 of a motor 84 so that rotation of pulley 80 by motor 84 will cause cable 52 to move within sleeve 54. The end of cable 52 is attached by fitting 81 to the wall of housing 70. Thus, slack at the end of cable 52 is formed when pulley 80 rotates in one direction but this slack is taken up when pulley 80 rotates in the other direction. This provides an additional stop to prevent pulley 80 from rotating too far. Cable 52 is also attached to pulley 80 so that it will not slide when pulley 80 rotates.

Attached to cable 52 within control housing 70 are limit taps 86 and 88. Positioned between limit taps 86 and 88 is a pivotably mounted switch contact member 90 that has an opening 92 in the end through which cable 54 extends. Switch contact member 90 is pivotably supported by shaft 94 so that switch contact member 90 can pivot in either direction to contact limit switch 96 or limit switch 98 when cable 52 is moved and limit taps 86 or 88 contacts and pivots switch contact member 90.

Figure 11:
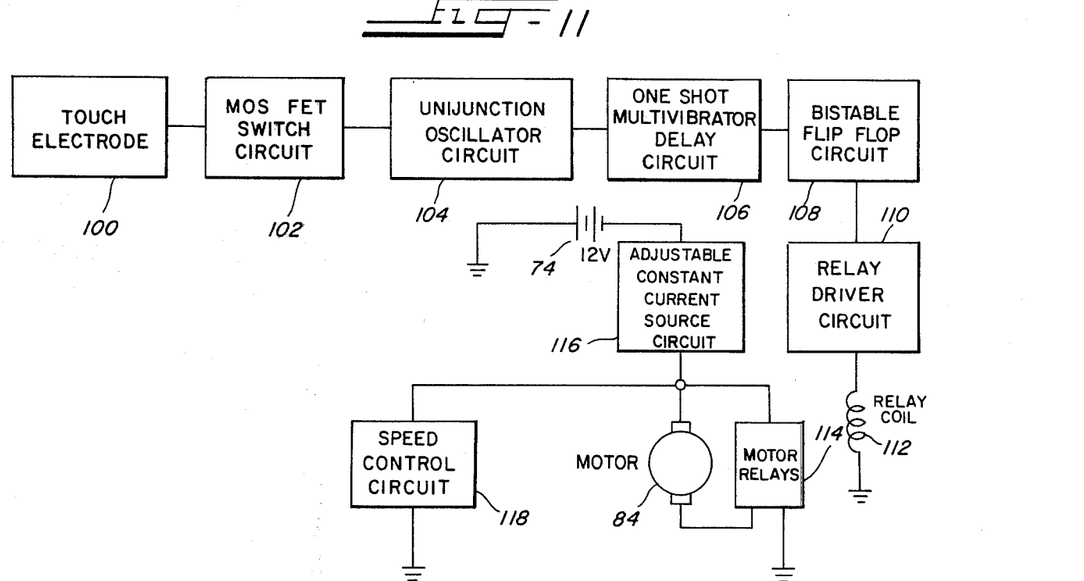
FIG. 11 is a block diagram of the control circuitry of the present invention.

With reference to FIG. 11, a block diagram of the control circuitry of the present invention is illustrated. A touch electrode 100 (attached to the arm rest of wheelchair 72 in FIG. 9) is connected to a MOS field effect transistor (FET) switch circuit 102 so that touch contact of the touch electrode with the arm of the patient causes the MOS FET switch circuit 102 to cause unijunction oscillator circuit 104 to commence oscillation. The electrical oscillations from unijunction oscillator circuit 104 are applied to the input of a one shot multivibrator delay circuit 106 that permits an adjustable two to seven second delay before one shot multivibrator delay circuit 106 applies a delayed transition signal to bistable flip-flop circuit 108. Upon receipt of a signal from the one shot multivibrator circuit 102, bistable flip-flop circuit 108 flips so that either a voltage signal is applied to relay driver circuit 110, or no signal is applied. Bistable flip-flop circuit 108 performs a memory function and holds the condition applied to relay driver circuit 110 until a subsequent contact is made with touch electrode 100 by the arm of the patient. Relay driver circuit 110 controls current flow through the relay coil 112 which in turn controls motor relays 114 which operate to reverse the polarity of voltage on the motor 84 to control the direction of rotation of motor 84.

An adjustable constant current source circuit 116 is provided to enable adjustment of the current to motor 84 which controls the force of motor 84 and in turn the torque/force of the closing fingers of the patient. Battery 74 provides power for motor 84 as well as the various circuits.

In addition, a speed control circuit 118 is provided that controls the magnitude of the voltage on motor 84 so that the closure time of the fingers of the patient can be adjusted for the convenience of the patient.

Figure 12:
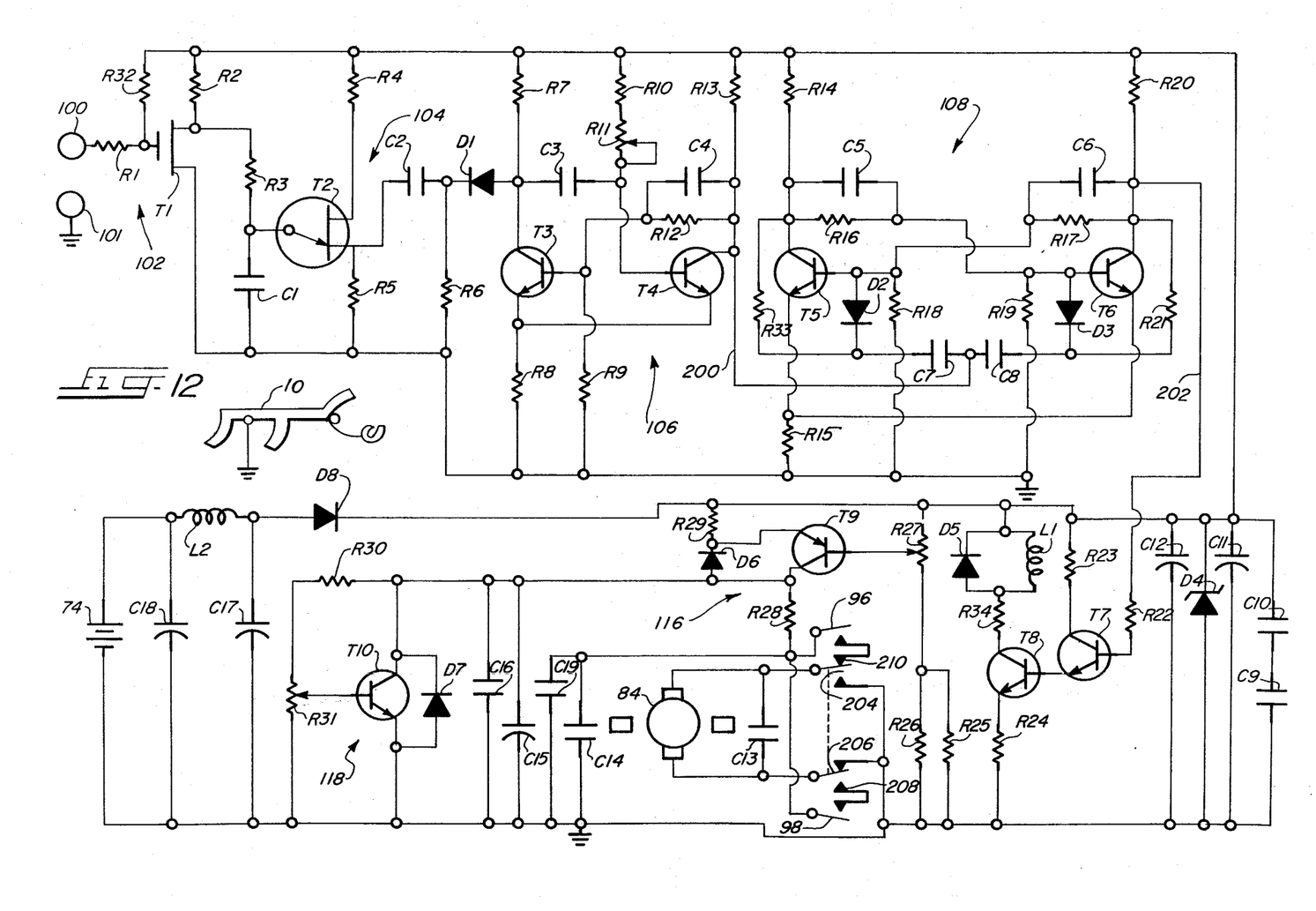
FIG. 12 is a schematic diagram of the control circuitry of the present invention.

More specifically, with reference to FIG. 12, a complete circuit diagram of the control circuitry of the present invention is illustrated. Touch electrode 100 is connected through resistor R-1 to the base of field effect transistor FET T-1 that comprises MOS FET switch circuit 102. Electrode 101 is also illustrated as connected to ground. Thus, when the patient contacts both electrodes 100 and 101 with his arm, current flows through resistor R-32 and R-1 and the patient's arm to ground biasing FET T-1 off. Alternatively, electrode 101 can be eliminated and arm splint 10 can be connected to ground so that the patient can contact electrode 100 with arm splint 10 to bias FET T-1 off. This latter arrangement is beneficial in those instances where the patient's arm is covered with talcum powder or other medication which might interfere with current flow through the skin. However, the current through the patient's arm is in the magnitude of eight microamps maximum, and thus, no discomfort or hazard is experienced by the patient.

The biasing off of FET T-1 results in unijunction transistor T-2 being biased on. Resistor R-2 and R-3 connect the base of unijunction transistor T-2 to the positive side of battery 74 and capacitor C-1 connects the base to ground. Unijunction transistor T-1 and resistor R-4 and R-5 comprise unijunction oscillator circuit 104 which commences oscillation when unijunction transistor T-1 is biased on. The oscillatory pulses of unijunction transistor T-2 are differentiated by capacitor C-2 and resistor R-6, and the negative edge of this differentiated signal is applied through diode D-1 to the collector of transistor T-3. Transistor T-3 and T-4, resistors R-7, R-8, R-9, R-10, R-11, R-12, R-13, and capacitors C-3, C-4 comprise one shot multivibrator delay circuit 106. Thus, the negative edge of the input signal from unijunction transistor T-2 causes this one shot multivibrator circuit to provide an essentially square wave output pulse at the collector of transistor T-4 on conductor 200. The width of the square wave pulse can be varied by adjusting variable resistor R-11 so that the width of the output pulse from transistor T-4 can be varied from approximately two to seven seconds.

The output of the one shot multivibrator circuit 106 is connected by conductor 200 to the input of bistable flip-flop circuit 108 comprising transistors T-5 and T-6, resistors R-14, R-15, R-16, R-17, R-18, R-19, R-20, R-21, and R-33, and capacitors C-5, C-6, C-7, and C-8. Bistable flip-flop circuit 108 operates as a conventional flip-flop circuit to alternatively switch transistors T-5 and T-6 from a conducting to a non-conducting state in response to receipt of the negative transition of the input signal from the one shot multivibrator delay circuit 106. Thus, upon receipt of the negative transition of the input pulse from the one shot multivibrator delay circuit 106, transistor T-6 switches either from a conducting to a non-conducting state or from a non-conducting to a conducting state depending upon the condition of transistor T-6 at the time of receipt of the input signal.

The collector of transistor T-6 is connected through conductor 202 to the base of transistor T-7. Thus, when transistor T-6 switches to a non-conducting state, the output voltage on line 202 is well above ground and is approximately seven volts. This voltage biases transistor T-7 to a conducting condition. However, when transistor T-6 is flipped to a conducting state, the voltage on conductor 202 is almost at ground potential since a direct circuit is formed through transistor T-6 through resistor R-15 to ground. In this condition, the voltage on conductor 202 is below cutoff of transistor T-7 and transistor T-7 switches to a non-conducting state.

The emitter of transistor T-7 is connected to the base of transistor T-8 so that when transistor T-7 is biased on, transistor T-8 will likewise be biased to a conducting condition so that current will flow through resistor R-24, transistor T-8, resistor R-34, and relay coil L-1. Transistors T-1 and T-8 comprise relay driver circuit 110. Diode D-5 is connected in parallel with relay coil L-1 to prevent transients. The flow of current through relay coil L-1 causes motor relay switches 204 and 206 to switch to a position opposite that shown in FIG. 12 to reverse the polarity of the voltage across the armature of motor 84. Thus, when current is flowing through relay coil L-1, the polarity on the armature of motor 84 is in one direction, and when the current is not flowing through relay coil L-1, the motor relay switches 204 and 206 return to the position illustrated in FIG. 12 so that the polarity on armature of motor 84 is in the opposite direction.

A zenor diode D-4 is connected from the positive side to the ground side of the circuit so that the voltage can be zenored down to a level that prevents pulse triggering of the control circuitry as a result of transients experienced during the start of operation of the motor 84. Capacitors C-9, C-10, C-11 and C-12 are provided to provide filtering of the DC voltage of the circuit.

Limit switches 96 and 98 are connected in series with the motor relay switches 204 and 206 respectively. Limit switches 96 and 98 are normally closed switches (but are shown open in FIG. 12) so that if limit switch 96 is opened when relay switch 204 is in a position contacting contact 210 (as shown in FIG. 12), the circuit to the armature of motor 84 is broken thereby stopping motor 84. However, if relay coil L-1 switches switches 204 and 206 so that switch 206 is contacting contact 208 to reverse the direction of motor 84 this circuit will be broken if limit switch 98 is opened.

Transistor T-9, resistors R-27, R-28, R-29 and diode D-6 form adjustable constant current source circuit 116. The torque of motor 84 is directly proportional to the current flowing through transistor T-9 and resistor R-28. This current can be adjusted to vary the torque of motor 84 by varying the bias potential on the base of transistor T-9 by adjusting variable resistor R-27. This circuit protects motor 84 and prevents excessive currents from flowing through the armature of motor 84. Also, this circuit provides a means to vary the prehensile forces applied to the fingers of the patient.

Capacitor C-13 across the armature of motor 84 suppresses transients during operation of the motor. Capacitors C-14, C-15, C-16 and C-19 are provided for filtering purposes.

Transistor T-10, diode D-7, resistors R-30 and R-31 provide an adjustable speed circuit 118 for motor 84. By adjusting the bias on the base of transistor T-10 by varying variable resistor R-31, the maximum voltage across the armature of motor 84 can be adjusted. Thus, since the speed of motor 84 is proportional to the voltage across the armature of motor 84, this circuit permits adjustment of the speed of the motor.

Diode D-8 is inserted in the circuit to prevent damage to the circuit in case battery 74 is accidentally inserted in the circuit with reverse polarity. Coil L-3 is a Pi filter to filter out transients from the motor driving the wheelchair to which the present invention is typically attached. Without coil L-2, transient voltage surges resulting during the operation of the wheelchair motor could trigger the operation of the control circuitry.

To operate the present invention, the patient contacts electrodes 100 and 101 with his arm or alternatively, contacts electrode 100 with arm splint 10 so that FET transistor T-1 is biased off. This causes unijunction transistor T-2 to oscillate as previously described which in turn causes the one shot multivibrator circuit to provide an adjustable two to seven second output pulse to the bistable flip-flop circuit 108. The negative transition of the output of the one shot multivibrator delay circuit 106 causes the bistable flip-flop circuit 108 to reverse its output state. For the purposes of explanation, it will be assumed that transistor T-6 was in a conducting state at the time that the patient contacted electrode 100. Thus, transistors T-7 and T-8 would be biased off. However, when transistor T-6 flips to the non-conducting state upon receipt of the negative transition of the input pulse from the one shot multivibrator delay circuit 106, transistors T-7 and T-8 are biased to a conducting state thereby causing current to flow through relay coil L-1 switching motor relay switches 204 and 206 to the opposite position shown in FIG. 12. Since limit switch 98 is normally closed, current will flow through limit switch 98, contact 208, switch 206 to the armature of motor 84 causing motor 84 to rotate.

With reference to FIG. 10, rotation of motor 84 rotates pulley 80 so that cable 52 moves toward the left as viewed in FIG. 10 causing tap 86 to pivot switch contact member 90 until it engages and opens switch 98 thereby interrupting the power to motor 84 and stopping rotation of pulley 80. The movement of cable 52 allows the cable 52 to move through sleeve 54 so that it causes annular member 42 to pivot finger trough member 44 so that the fingers of the patient move toward the thumb to provide finger prehension to the patient. Thus, the patient's fingers are closed. To open the patient's fingers, the patient once again contacts electrode 100 causing the same operation of FET T-1, unijunction transistor oscillator T-2 and the one shot multivibrator delay circuit 106. The output pulse from the one shot multivibrator delay circuit 106, causes transistor T-6 to flip back to its original conducting condition thereby biasing transistors T-7 and T-8 off interrupting current to relay coil L-1. Motor relay switches 204 and 206 then switch back to the position shown in FIG. 12 reversing the polarity of voltage on motor 84 thereby reversing the direction rotation of the motor 84. This causes motor 84 to pivot pulley 80 in the opposite direction so that cable 52 moves towards the right as viewed in FIG. 10 until tap 88 moves switch contact member 90 until it opens limit switch 96 interrupting power to motor 84. This motion of cable 52 allows spring 46 to open the fingers of the patient.

Thus, if the patient wishes to grasp an object, the patient contacts the touch electrode 100 thereby initiating operation of the control circuitry. However, the patient has a two to seven second delay depending on the adjustment of resistor R-11 in which to maneuver the arm and hand to a position ready for grasping the desired object. The motor is then powered as previously described causing prehension of the patient's fingers towards the thumb so that the object is grasped between the fingers and thumb. To release the object, the patient once again contacts touch electrode 100 and then maneuvers the arm and hand to the desired position for release of the object.

The present invention is particularly advantageous for cervical 6- cervical 7 motor lesion quadraplegics who have partial motor control of the arms but lack motor control of the hands and fingers. Typically, such a quadraplegic is equipped with a battery power driven wheelchair for movement. Thus, the touch electrode 100 can be attached to the arm rest of the wheelchair, and the twelve volt battery utilized to drive the wheelchair can also be utilized to power the control circuitry and the motor 84. Further, the touch electrode is contact sensitive and requires no force from or complicated muscular articulation by the patient to initiate operation of the control circuitry. A further advantage of the present invention is that the patient can use the same arm to which the orthosis is attached to initiate operation of the orthosis thereby permitting the patient to be equipped with an orthosis for each arm.

The time delay provided by the one shot multivibrator circuit also provides the advantage of allowing the patient to initiate operation of the control circuitry and then maneuvering the arm and hand to a position ready for grasping or releasing an object.

Typical values of the various components in the control circuitry illustrated in FIG. 12 are as follows.

```
R-1  - 1 meg. ohms        R-12 - 35 K ohms         R-23 - 2200 ohms
R-2  - 470 ohms           R-13 - 10 K ohms         R-24 - 10 ohms
R-3  - 10 K ohms          R-14 - 1 K ohms          R-25 - 100 ohms
R-4  - 1 K ohms           R-15 - 1 K ohms          R-26 - 100 ohms
R-5  - 1100 ohms          R-16 - 4.7 K ohms        R-27 - 50 ohms
R-6  - 100 K ohms         R-17 - 4.7 K ohms        R-28 - 1 ohms
R-7  - 10 K ohms          R-18 - 3.3 K ohms        R-29 - 1 ohms
R-8  - 1 K ohms           R-19 - 3.3 K ohms        R-30 - 50 ohms
R-9  - 25 K ohms          R-20 - 1 K ohms          R-31 - 100 ohms
R-10 - 5 K ohms           R-21 - 100 K ohms        R-32 - 240 meg. ohms
R-11 - 50 K ohms          R-22 - 47 K ohms         R-33 - 100 K ohms C-1 - 10 microfarads      C-8  - .02 microfarads   C-14 - 100 microfarads
C-2 - .01 microfarads     C-9  - .47 microfarads   C-15 - 100 microfarads
C-3 - 100 microfarads     C-10 - .47 microfarads   C-16 - .47 microfarads
C-4 - 370 microfarads     C-11 - 100 microfarads   C-17 - 100 microfarads
C-5 - 370 microfarads     C-12 - 100 microfarads   C-18 - 100 microfarads
C-6 - 370 microfarads     C-13 - 4 microfarads     C-19 - .47 microfarads
C-7 - .02 microfarads L-2 - 10 microhenries T-1 - 2N3747              T-9  - 2N1544
T-2 - 2N4871              T-10 - 2N3055
T-3, 4, 5, 6, 7, 8 - 2N696

D-1, 2, 3, 5, 6, 7 - 1N4003    D-8 - 1N1613
```

It should be expressly understood that various alterations, changes and modifications can be made to the embodiment illustrated herein without departing from the spirit and scope of the present invention as defined in the appended claims.

We claim:

1. An orthosis comprising, in combination:
   prehension means for providing grasping capability in conjunction with a disabled extremity of the body of a patient and adapted for attachment to said extremity;
   drive means operatively connected to said prehension means and adapted to provide operative prehensile force to said prehension means;
   a power source;
   control means comprising:
   electronic switch means for switching to provide a switch signal in response to touch contact by the patient of a touch sensitive contact means;
   oscillator means for oscillating in response to receipt of the switch signal from said electronic switch means;
   delay means for providing a time delayed signal in response to oscillation of the oscillator means;
   flip-flop means for providing and maintaining a relay signal in response to receipt of the time delayed signal;
   relay means for providing a direction of operation signal to said drive means in response to receipt of the relay signal.

2. An orthosis, as claimed in claim 1, wherein said prehension means comprises:
   an arm trough member dimensioned and adapted to attach to the forearm of the patient;
   a hand trough member adjustably attached to said arm trough member, dimensioned and adapted to attach to the hand of the patient; said hand trough member including a thumb trough flange for retaining the thumb of the patient;
   a finger trough member pivotably attached to said hand trough member dimensioned and adapted to retain at least one finger of the patient; said finger trough member being operably connected to said drive means so that said drive means can cause said finger trough member to pivot to bring the finger and thumb of the patient into and out of contact with one another so that the patient can grasp and release objects.

3. An orthosis, as claimed in claim 2, wherein said hand trough member is adjustably attached to said arm trough member by a retaining means for holding said hand trough member in a fixed angular orientation with respect to said arm trough member when tightened and for loosening so that the angular orientation between said hard trough member and said arm trough member can be adjusted for the comfort of the patient.

4. An orthosis, as claimed in claim 1, wherein said drive means comprises an electric motor.

5. An orthosis, as claimed in claim 1, wherein said power source comprises a portable battery.

6. An orthosis, as claimed in claim 1, wherein said control means further comprises:
   adjustable constant current means for adjusting the magnitude of the operative forces applied by said drive means; and
   speed control means for controlling the speed of operation of said drive means.

7. An orthosis, as claimed in claim 5, wherein said control means further comprises limit switch means for limiting the duration of operation of said drive means.

8. An orthosis, as claimed in claim 5, wherein said portable battery is a twelve volt car battery mounted on a battery driven wheelchair.

9. A hand orthosis for providing finger prehension for a quadraplegic patient having partial motor control of the arms and lacking motor control of the hands and fingers comprising:
   arm splint means for attachment to the patient's forearm including:
   thumb flange means for retaining the patient's thumb;
   finger trough means for retaining at least one finger of the patient, said finger trough means adapted to close toward and open away from the thumb flange means to provide finger prehension so that the patient can grasp and release objects;

drive means operably connected to said arm splint means for causing said finger trough means to close and open to provide prehensile force;

control means for controlling the operation of said drive means comprising:

electronic switch means for switching to provide a switch signal in response to touch contact by the patient of a touch sensitive contact means;

oscillator means for oscillating in response to receipt of the switch signal from said electronic switch means;

delay means for providing a time delayed signal in response to oscillation of the oscillator means;

flip-flop means for providing and maintaining a relay signal in response to receipt of the time delayed signal;

relay means for providing a direction of operation signal to said drive means in response to receipt of the relay signal;

a power source means for providing electrical power to said drive means and said control means.

10. A hand orthosis, as claimed in claim 9, wherein said drive means comprises an electric motor.

11. A hand orthosis, as claimed in claim 9, wherein said power source means comprises a portable electric battery.

12. A hand orthosis, as claimed in claim 9, wherein said arm splint means further includes:

an arm trough member dimensioned and adapted to attach to the forearm of the patient;

a hand trough means adjustably attached to said arm trough member dimensioned and adapted to attach to the hand of the patient; said thumb flange means being attached to said hand trough member and said finger trough means being pivotably attached to said hand trough member.

13. A hand orthosis, as claimed in claim 12, wherein said hand trough member is adjustably attached to said arm trough member by a retaining means for holding said hand trough member in a fixed angular orientation with respect to said arm trough member when tightened and for loosening so that the angular orientation between said hand trough member and said arm trough member can be adjusted for the comfort of the patient.

14. A hand orthosis for providing finger prehension for a quadraplegic patient having partial motor control of the arms but lacking motor control of the hands and fingers comprising:

an arm trough member for being attached to the forearm of the patient;

a hand trough member for being attached to and supporting the hand of the patient, said hand trough member adjustably mounted to the arm trough member so that the angular orientation between the hand member and the arm trough member can be varied;

a thumb flange member attached to the hand trough member for supporting and retaining the patient's thumb;

a finger trough member for supporting and retaining at least one of the patient's fingers, said finger trough member being pivotably attached to the hand trough member so that said finger trough member can pivot to close the fingers of the patient toward the thumb of the patient so that the patient can grasp objects and open the fingers of the patient away from the thumb of the patient so that the patient can release objects;

an electric motor;

a pulley mounted on said motor;

a cable connected at one end to said pulley and connected at the opposite end to the finger trough member so that rotation of said pulley in one direction causes said finger trough member to pivot in a direction to close the patient's fingers and rotation of said pulley in an opposite direction causes finger trough member to pivot in a direction to open the patient's fingers;

a touch sensitive contact;

an electronic switch means connected to said contact for providing a switching signal in response to touch contact of touch sensitive contact by the arm of the patient;

an oscillator means for oscillating in response to receipt of the switching arm;

a delay means for providing a time delayed signal in response to oscillation of said oscillator means;

a memory means for receiving the time delayed signal and providing and maintaining a relay signal in response to receipt of the time delayed signal;

relay means for providing voltage to said motor in a first polarity to cause said motor to rotate in a first direction in response to receipt of the relay signal, and for providing voltage to said motor in an opposite polarity to cause said motor to rotate in an opposite direction in response to receipt of a subsequent relay signal, whereby touch contact by the patient of the touch sensitive contact means causes the fingers of the patient to close to grasp objects and subsequent touch contact by the patient of the touch sensitive contact means causes the fingers of the patient to open to release objects.

15. A hand orthosis, as claimed in claim 14, wherein said electronic switch means comprises a field effect transistor.

16. A hand orthosis, as claimed in claim 14, wherein said oscillator means comprises a unijunction transistor oscillator.

17. A hand orthosis, as claimed in claim 14, wherein said delay means comprises a one shot multivibrator that provides a pulse having an adjusting means for adjusting the time duration of the pulse from two to seven seconds.

18. A hand orthosis, as claimed in claim 17, wherein said memory means comprises a bistable flip-flop circuit that changes output states in response to receipt of the negative transition of the pulse from said one shot multivibrator.

19. A hand orthosis, as claimed in claim 14, further comprising: adjustable constant current means for providing a constant current to said motor so that the torque of said motor can be adjusted.

20. A hand orthosis, as claimed in claim 14, further comprising: speed control means for adjusting the voltage applied to said motor so that the speed of rotation of said motor can be adjusted.

* * * * *